United States Patent [19]

Chapoteau et al.

[11] Patent Number: 4,810,351
[45] Date of Patent: Mar. 7, 1989

[54] CARBONATE SELECTIVE MEMBRANE AND ELECTRODE

[75] Inventors: Eddy Chapoteau, Monsey; W. James Scott, Croton-on-Hudson, both of N.Y.

[73] Assignee: Technicon Instruments Corporation, Tarrytown, N.Y.

[21] Appl. No.: 41,391

[22] Filed: Jun. 1, 1987

Related U.S. Application Data

[63] Continuation of Ser. No. 908,745, Sep. 18, 1986, abandoned.

[51] Int. Cl.[4] .................................................. G01N 27/46
[52] U.S. Cl. ..................................... 204/418; 204/1 T
[58] Field of Search .................. 204/1 T, 1 K, 416, 418

[56] References Cited

U.S. PATENT DOCUMENTS

| | | | |
|---|---|---|---|
| 3,706,649 | 12/1972 | Cosgrove et al. | 204/418 |
| 3,723,281 | 3/1973 | Wise | 204/417 |
| 3,898,147 | 8/1975 | Niedrach | 204/418 |
| 4,214,968 | 7/1980 | Battaglia et al. | 204/435 |
| 4,272,328 | 6/1981 | Kim et al. | 204/418 |
| 4,303,408 | 12/1981 | Kim et al. | 204/418 |

OTHER PUBLICATIONS

*Analytic Chimica Acta*, 76: pp. 155–164 (1975).
Greenberg et al, *Analytica Chimca Acta*, 141, pp. 57–64 (1982).
*Analytical Chemistry*, 54, pp. 423–429 (1982).
*Analytical Chemistry*, 53, pp. 588–593 (1981).

*Primary Examiner*—T. Tung
*Attorney, Agent, or Firm*—Jeffrey M. Greenman

[57] ABSTRACT

The carbonate ion selective membrane of the invention comprises (a) a polymeric inert support material; (b) a plasticizer effective to solubilize the support material; (c) a quaternary ammonium ion; (d) an ionophore which is preferentially reactive with carbonate ions; and (e) a hydrophobic molecule effective to exclude ions other than carbonate ions. The addition of a hydrophobic molecule to the membrane formulation serves two purposes. First, it assists in the "binding" of the organic constituents to the matrix. Second, it repels charged species, i.e., anions and cations, from the solution phase, thereby improving selectivity to the carbonate species which enters the membrane via selective complexation with the ionophore. The quaternary ammonium ion is preferably a $C_7$ to $C_9$ quaternary ammonium ion. In this case, the plasticizer is selected to be one effective to maximize the binding of carbonate ions with the $C_7 C_9$ quaternary ammonium ions. The invention further provides a carbonate ion selective electrode comprising an internal reference element in electrochemical contact with the membrane described above.

23 Claims, 1 Drawing Sheet

CARBONATE SELECTIVE MEMBRANE AND ELECTRODE

This is a continuation of application Ser. No. 908,745, filed Sept. 18, 1986 now abandoned.

BACKGROUND OF THE INVENTION

1. Field of the Invention

The present invention relates to the field of electrodes and ion selective membranes for use therewith, particularly those membranes and electrodes specifically responsive to carbonate ions such as are related to the carbon dioxide content of human blood, serum or plasma.

2. Brief Description of the Prior Art

The normal pH of plasma is 7.4 and defines the ratio of $HCO_3^-$ to $H_2CO_3$ (by the Henderson-Hasselbalch equation). Disturbances in blood pH are compensated by appropriate responses of the respiratory and renal systems. Hence, more than one analysis is required to determine acid-base status. One such determination is the analysis of the carbon dioxide content of the blood. Carbon dioxide dissolved in blood is in equilibrium between the interior of red blood cells and the plasma and also within the plasma. It is present as dissolved carbon dioxide ($CO_2$), carbonic acid ($H_2CO_3$), bicarbonate ($HCO_3^-$), carbonate ($CO_3^{-2}$) and carbonate bound to free amino groups of proteins ($RNHCOO^-$. The total concentration is defined as the sum of the concentrations of all forms in which $CO_2$ is present. In most methods for the determination of total carbon dioxide in blood, serum or plasma, the biological fluid is added to an acid reagent which converts bound $CO_2$ ($HCO_3^-$, $CO_3^{-2}$ and $RNHCOO^-$) into free $CO_2$ ($H_2CO_3$ and dissolved $CO_2$). As a measure of total carbon dioxide, one may employ extraction methods (e.g., dialysis) or equilibration methods, measuring increase in pressure of gas at a fixed volume. Potentiometric determination of the total $CO_2$ has been performed using carbonate ion-selective electrodes. This requires the fixing of the pH of the sample at a relatively high value by the addition of a buffered solution prior to testing, such as described in Herman and Rechnitz, Anal. Chim. Acta, 76:155–164 (1975).

Wise, U.S. Pat. No. 3,723,281, describes a bicarbonate ion sensitive electrode in which the ion sensing portion of the electrode is an organic solution containing a high molecular weight quaternary ammonium salt dissolved in dual solvent system consisting of a trifluoroacetyl-p-alkyl benzene and an alcohol of low water solubility. Electrodes of this sort which contain liquid-sensing components have shorter life spans and are less stable and selective than others in solid format which have more recently become known in the art.

Kim, et al, U.S. Pat. No. 4,272,328, describes an ion selective electrode multilayer analytical element which includes an ionophore-containing membrane and a buffer zone which comprises a hydrophilic binder and a buffer in an amount sufficient to control the pH of the solution as analyzed between about 7.5 to about 9.5. Under these conditions it is asserted that the element is comparatively less susceptible to the interfering effects of gentisate, salicylate and p-amino salicylate. Nowhere does this describe the avoidance of interference from species such as heparin or from large molecular weight molecules endogenous to serum such as free fatty acids, triglycerides or lipids. Apart from the separate buffer overcoat, it nowhere describes the use of particular molecules in the ionophore membrane effective to exclude ions other than carbonate ions to enhance selectivity. The only mention which is made of hydrophobic binders is with reference to the polyvinyl chloride used as the polymeric inert support material. The use of quaternary ammonium salts is generally discussed and examples are given only of quaternary salts in which the substitutions include lower alkyl constituents.

Avoidance of the effects of interfering species has been sought in various potentiometric determinations. For example, a chloride ion-selective electrode has been described which uses a solid polymer membrane. The membrane is essentially a plasticized polystyrene film with a proper quaternary ammonium ion and also includes an appropriate sulfonic acid group in order to repel anions other than chloride. See, Oka, et al, Anal. Chem. 53:588–593 (1981).

Meyerhoff, et al, *Anal. Chim. Acta*, 141:57–64 (1982) describe a carbonate selective polymeric membrane Aliquat 336, the ionophore is trifluoroacytl-p-butylbenzene, and the plasticizer is either di-(2-ethylhexyl) sebazene, and the plasticizer is either di-(2-ethylhexyl) sebacate or di-octyl phthalate and the polymeric inert support material is poly (vinyl chloride). The data reported in this publication provide a relatively slow response time, particularly as shown in FIG. 4 thereof, and relatively significant effects of interference from salicylate.

A recent publication, Simon, et al, Anal. Chem., 54:423–429 (1982) describes a bicarbonate electrode which uses ethanolamines as ion-exchangers, but interference from the biologically common chloride anion is present. The device has excessively long response times (5–15 minutes).

In summary, potentiometric sensors have been designed to avoid interference from like-charged ions by incorporating ionized species into the membrane body. These serve to physically repel the interfering ions from the membrane body and thereby minimize their effect on the development of the electrode potential. Layered structures may act as diffusion barriers to interfering species (e.g., via adsorption) but response time is necessarily slow.

SUMMARY OF THE INVENTION

In contrast to the prior art described above and in accordance with the present invention, a carbonate ion-selective membrane and electrode incorporating such membrane has been provided which is relatively less susceptible to interference from serum and plasma components such as free fatty acids, heparin, salicylate and the like, and which provides a response stability permitting a faster sampling rate.

The carbonate ion selective membrane of the invention comprises (a) a polymeric inert support material; (b) a plasticizer effective to solubilize the support material; (c) a quaternary ammonium ion; (d) an ionophore which is preferentially reactive with carbonate ions; and (e) a hydrophobic molecule effective to exclude ions other than carbonate ions. The addition of a hydrophobic molecule to the membrane formulation serves two purposes. First, it assists in the "binding" of the organic constituents to the matrix. Second, it repels charged species, i.e., anions and cations, from the solution phase, thereby improving selectivity to the carbonate species which enters the membrane via selective complexation with the ionophore. The quaternary ammonium ion is preferably a $C_7$ to $C_9$ quaternary ammonium ion. In this case, the plasticizer is selected to be one effective to maximize the binding of carbonate ions with the $C_7$ to $C_9$ quaternary ammonium ions.

The invention further provides a carbonate ion selective electrode comprising an internal reference element in electrochemical contact with the membrane described above. This electrode can take any of a variety of physical formats including the now recognized multilayer analytical element format, as well as more conventional electrode configurations.

DESCRIPTION OF THE PREFERRED EMBODIMENTS

Figure 1:
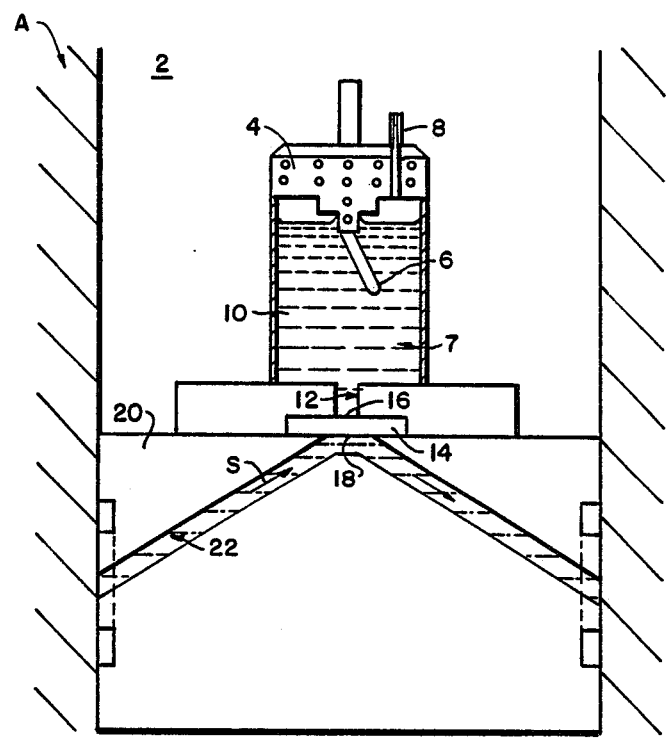
FIG. 1 is a schematic illustration of a flow-through electrode assembly suitable for incorporation of the membrane of the invention.

The present invention provides a carbonate selective membrane particularly useful in electrodes adapted for use with continuous flow or dry phase analytical systems. Such electrodes are commonly used in carrying out assays on liquid media. The liquid media to be assayed can be naturally occurring or artificially formed liquids containing carbon dioxide for which the total concentration of carbon dioxide species is sought. These are usually aqueous or a biological fluid or dilution thereof. Such biological fluids that can be assayed include serum, plasma and amniotic fluids.

The membrane of the invention comprises a dimensionally stable matrix formed of a polymeric inert support material. The polymeric inert support material is usually a vinyl chloride polymer, preferably a very high molecular weight vinyl chloride homopolymer (greater than about 140,000 molecular weight) such as poly (vinyl chloride). The polymeric inert support material can be selected from any other material which imparts the desired dimensionally stable characteristics suitable for handling and use of the membrane, particularly in conjunction with the electrode.

The plasticizer used in accordance with the invention is preferably an adipate. Most preferred among such adipates is di-(2-ethylhexyl) adipate. Additional adipates which are suitable for use include diisobutyl, dipentyl, didecyl, diethoxyethyl, dioctyl, diallyl, diisooctyl or dibutyl adipate.

Ion-selective electrodes respond only to ionic entities. The ionic forms of carbon dioxide are bicarbonate ($HCO_3^-$) and carbonate ($CO_3^{-2}$). The appropriate ionophor must be such that it complexes or interacts with such species. One would expect such a phenomenon to occur with a positively charged moiety, or with one which is polarized in a positive direction or which interacts with the anion via, for example, hydrogen bonding. Note that in addition to performing the desired function, the ionophore should be soluble in the matrix, e.g., plasticized PVC but have a minimal solubility in the aqueous phase. The best molecules then will be relatively large ones which contain, for example, a carbonyl group, preferably one with an electron withdrawing function directly attached to the carbon atom of the functional group. Ionophores suitable for use with the invention are those known to the prior art including higher alkyl-substituted fluoroacetophenone, preferably para- or ortho-substituted. Such higher alkyl fluoroacetophenones are preferably $C_{10}$–$C_{20}$ fluoroacetophenones. Preferred examples of such fluoroacetophenones are those selected from the group consisting of alpha-substituted trifluoroacetophenones, such as p-butyl-alpha, alpha, alpha-trifluoroacetophenone. Even more desirable is the use of p-decyl-alpha, alpha, alpha-trifluoroacetophenone. The more hydrophobic the trifluoroacetophenone molecule is the less drift is observed in the response, particularly in very fast flowing continuous flow analysis systems.

The membrane further includes a hydrophobic molecule effective to exclude ions other than carbonate ion. This hydrophobic molecule included in addition to the above components is at least a $C_{10}$ hydrocarbon which can optionally be hetero atom substituted. Preferred examples of this hydrophobic molecule are 1-phenyldecane, diphenyl ethers, dodecanes, butylbenzenes and other alkyl or aryl hydrocarbons of sufficient size.

Optionally included in the membrane as a charge carrier is a tetra-$C_7$-$C_9$ quaternary ammonium ion. This molecule, therefore, includes four large groupings bonded to the nitrogen, e.g., those having the same or different hydrocarbon chains all being within the $C_7$-$C_9$ hydrocarbon range. Preferably the $C_7$-$C_9$ hydrocarbons on any ammonium are the same. Particularly desirable is tetra-n-octyl ammonium. Hydrocarbon chain lengths smaller than these have a tendency to leach out of the membrane and chains longer than those set forth do not result in improved selectivity, probably due to a decrease in steric hindrance of interfering ion association with the charge carrier.

Membrane formulations can be provided in which each component is provided in a range which is preferred. For example, a preferred membrane formulation comprises the following components within the percentage (weight/weight) range as follows: tetra octyl ammonium bromide (5–10); di-(2-ethylhexyl) adipate (30–45); p-decyl-alpha, alpha, alpha-trifluoroacetophenone (16–20); poly (vinyl chloride) (15–50); and 1-phenyldecane (5–10).

FIG. 1 illustrates a flow through electrode assembly A. It includes an electrode housing 2 having an electrode base 4 which positions an internal reference element 6, usually a silver/silver chloride wire. Internal reference electrode 6 extends out of electrode housing 2 to components (not shown) used in comparison and data reporting. Reference electrode 6 is free standing in reference electrolyte chamber 7. Reference electrolyte chamber 7 has a filling port 8 through which electrolyte solution 10 is introduced from an external source (not shown). Electrolyte solution 10, shown in chamber 7 covering element 6, establishes fluid and electrolytic contact between element 6 and membrane orifice 12.

Membrane 14 has upper surface 16 and lower surface 18. Membrane upper surface 16 covers the opening of orifice 12 and, as such, is in fluid and electrolytic contact with electrolytic solution 10. Membrane 14 is prepared as described elsewhere herein and is formulated, in accordance with the invention, to permit preferential introduction therein of carbonate ions over anionic species.

Conduit block 20 is mounted against electrode housing 2. Conduit 22 provides a passageway for the flow of sample S fluids through conduit block 20. Sample S is in fluid and electrolytic contact with membrane lower surface 18. Carbonate ions in sample S enter into membrane 14 and the concentration thereof is measured free of interference from other anions.

EXAMPLE I

The experiments reported by this example compare the susceptibility to salicylate interference of electrodes provided with membranes having different charge carriers and plasticizers.

The membranes were made as follows. Four 6 ml aliquots of tetrahydrofuran (Burdick and Jackson Laboratories, Jackson, Mich., Catalog #340), each containing 109-306 mg of polyvinyl chloride (Scientific Polymer Products, Ontario, N.Y., Catalog #PVC 038) and 116-145 mg of p-butyl, alpha, alpha, alpha-trifluoroacetophenone (Specialty Organics, Inc., Irwindale, Calif.), were prepared and combined, respectively, with:

(1) 36-73 mg Aliquat 336 (Henkel Corp., Kankakee, Ill.) and 218-327 mg di-(2-ethylhexyl) sebacate (Polyscience, Inc., Warrington, Pa., Catalog #2222);

(2) 36-73 mg trioctylpropyl ammonium chloride, (Eastman Kodak Co., Rochester, N.Y., Catalog #P10341); and 218-327 mg di-(2-ethylhexyl) sebacate;

(3) 36-73 mg tetraheptyl ammonium chloride (Eastman Kodak, supra, Catalog #9505) and 218-327 mg di-(2-ethylhexyl) sebacate;

(4) 36-73 mg tetraheptyl ammonium chloride and 218-327 mg di-(2-ethylhexyl) adipate (Scientific Polymer Products, supra, Catalog #P-132).

Each solution was decanted into a separate 30 ml beaker which was then covered with a sheet of filter paper weighted with a glass stopper (to keep out dust and dirt particles) and placed in an operating fume hood overnight for the tetrahydrofuran to evaporate, leaving a clear, durable membrane sheet on the bottom of the beaker. Each sheet so formed was removed with tweezers and circular sections of approximately 5.0 mm diameter were cut out to provide individual ion-selective membrane discs. The individual membrane discs were mounted on a Technicon flow through electrode assembly (Technicon Instruments Corporation, Tarrytown, N.Y., Part #023-B044-01 comprising an upper housing, Part #023-B043-01) which forms the internal reference compartment and is filled with a solution of 0.1 molar potassium chloride. Alternatively, mixtures of potassium chloride and bicarbonate (sodium or potassium) can be used. This potassium chloride solution is in contact with an internal silver-silver chloride reference electrode and the upper surface of the ion-selective membrane. A lower block (Technicon, supra, Part #023-0078-01) carries the sample and brings it into contact with the bottom surface of the ion-selective membrane. The flow through electrode assembly noted above was attached to a counter-flow reference block (Technicon, supra, Part #044-B082-01) which supports a silver-silver chloride reference electrode (Technicon, supra, Part #044-B079-01). Outputs from both electrodes are fed to a SMAC amplifier (Technicon, supra, Part #203-B033-01) and the amplified difference in signal is fed to a YEW-type 3056 recorder (Yokogawa Electric Works, Ltd., Shenandoah, Ga.). The continuous flow assembly is fed with counter-flow reference solution and with sample mixed with buffer at a 1 to 10 dilution ratio at a sampling rate of 120 samples per hour on a continuous flow system. The buffer is of pH greater than 8.2 in order to produce carbonate ions when mixed with the sample, and contains a mercury complexone with ethylenediamine tetraacetic acid. The mercury complexone is added equally to each analysis and reduces the magnitude of potential anionic interferences (Kumar, U.S. Pat. No. 4,196,056).

The electrodes prepared above were calibrated using aqueous 15 and 50 mM sodium bicarbonate standards. The standards also contained 100 mM sodium chloride. Sodium salicylate (interfering species) was added to a solution of 30 mM sodium bicarbonate and 100 mM sodium chloride to give a final concentration of 8 mg/dl of sodium salicylate. A like solution, free from salicylate, was used as a control. Any interference (variation in signal from sodium salicylate compared to control) was reduced to an equivalent additional analytical concentration in mM using standard Nernst relationships.

Results $CO_2$ concentrations for each sample were observed. Observed concentrations greater than the reference concentration were due to salicylate interference. The relative levels of salicylate interference on electrodes using each of the membranes described above were as follows; membrane 1 (20 mM); membrane 2 (11 mM); membrane 3 (7 mM); and membrane 4 (4 mM)

These data show that larger alkyl functions comprising the quaternary alkyl ammonium ion-exchanger result in lower interference from salicylate than with smaller functions. Interference is further reduced using adipate plasticizer instead of sebacate.

EXAMPLE II

Various anionic species may be expected to interfere with carbon dioxide analyses using ion-selective membranes. The experiments described in this example provide data on the interference due to various anionic species when making measurements using an electrode having a membrane as disclosed herein in comparison to the same electrode having a membrane of standard formulation.

The membrane discs used in this Example were made according to the procedures and reagent amounts described in Example I. The membrane prepared using a formulation in accordance with the invention comprised PVC; p-decyl-alpha, alpha, alpha-trifluoroacetophenone (Trans World Chemicals, Inc., Washington, D.C.); tetraoctylammonium bromide (Fluka Chemical Corp., Hauppauge, N.Y., Catalog #88000); di-(2-ethylhexyl) adipate; and 1-phenyldecane (Aldrich Chemical Co., Milwaukee, Wis.). The membrane prepared using a formulation in accordance with the prior art comprised PVC; p-butylalpha, alpha, alpha-trifluoroacetophenone; Aliquat 336 as ionexchanger; and di-(2-ethylhexyl) sebacate as plasticizer.

After preparation, the individual membrane discs were each mounted on an electrode housing which was then positioned on a continuous flow station sampling at 120 samples per hour, using the conditions and reagents described in Example I.

The electrodes were calibrated using 15 and 50 mM aqueous sodium bicarbonate standards. Interfering substances were added to a 25 mM sodium bicarbonate solution, this solution being used as a control. The final concentrations of the interfering substances so added were: coumadin (2 mg/dl); sodium nitrate (5 mM); sodium bromide (10 mM); potassium iodide (10 mM); potassium cyanide (10 mM); sodium acetate (10 mM); sodium salicylate (16 mg/dl); sodium gentisate (16 mg/dl); sodium hypaque (65 mM); and lithium heparin (28 USP units/ml).

Results

When used in the analytical procedure described, the above membranes having the preferred formulation in accordance with the invention (IF) and those having the prior art standard formulation (SF) gave the following results (the data are reported for IF and SF, respectively, and are given as percentage positive error at the 25 mM level): coumadin (0.0 and 3.2); sodium nitrate (0.0 and 1.6); sodium bromide (1.2 and 1.6); potassium iodide (2.8 and 44.0); potassium cyanide (5.6 and 11.2); sodium acetate (0.0 and 1.6); sodium salicylate (2.4 and 78.4); sodium gentisate (2.4 and 8.0); sodium hypaque (6.0 and 9.6); and lithium heparin (0.0 and 9.6).

These data show that the preferred formulation (IF) in all cases performs at a level superior to the standard formulation, (SF) most markedly in the presence of salicylate and iodide. Also, it should be noted that a significant quantity of ingested salicylate (aspirin) is bound to protein and cannot interfere in this state. Thus, the salicylate interferences reported above were based on analyses of solutions containing greater levels of available salicylate than is commonly encountered. Note that performance is improved by the presence of the Hg (II) complexone in the reagent. Without it, the SF gives a positive percentage error of 16.8 for heparin, 116 for salicylate and 34 for cyanide.

EXAMPLE III

In the experiments reported by this example, membranes prepared without the addition of a suitable hydrophobic molecule, effective to exclude anions other than carbonate, were compared to determine if they showed greater interference from these ions.

The membrane discs used in this Example were made according to the procedures and reagent amounts described in Example I. The membrane prepared using a formulation in accordance with the invention comprised PVC; p-decyl-alpha, alpha, alpha-trifluoroacetophenone; tetraoctylammonium bromide; di-(2-ethylhexyl) adipate; and 1-phenyldecane. The membrane prepared using a formulation without a suitable hydrophobic molecule comprised PVC; p-decylalpha, alpha, alpha-trifluoroacetephenone; tetraoctylammonium bromide; and di-(2-ethylhexyl) adipate.

After preparation, the individual membrane discs were each mounted on an electrode housing which was then positioned on a continuous flow station sampling at 120 samples per hour, using the conditions and reagents described in Example I.

The electrodes were calibrated using 15 and 50 mM aqueous sodium bicarbonate standards. Interfering substances were added to a 25 mM sodium bicarbonate solution, this solution being used as a control. The final concentrations of the interfering substances so added were: coumadin (2 mg/dl); sodium nitrate (5 mM); sodium bromide (10 mM); potassium iodide (10 mM); potassium cyanide (10 mM); sodium acetate (10 mM); sodium salicylate (16 mg/dl); sodium gentisate (16 mg/dl); sodium hypaque (65 mM); and lithium heparin (28 USP units/ml).

Results

When used in the analytical procedure described, the above membranes having the preferred formulation in accordance with the invention (IF) and those without added hydrophobic species (OH) gave the following results (the date are reported for IF and OH, respectively, and are given as percentage positive error at the 25 mM level): coumadin (0.0 and 2.0); sodium nitrate (0.0 and 2.0); sodium bromide (1.2 and 1.2); potassium iodide (2.8 and 10.0); potassium cyanide (5.6 and 10.0); sodium acetate (0.0 and 1.2); sodium salicylate (2.4 and 30.8); sodium gentisate (2.4 and 5.6); sodium hypaque (6.0 and 10.1); and lithium heparin (0.0 and 0.0).

These data show that the preferred formulation (IF) in the majority of cases performs at a level superior to the comparison formulation, most markedly in the presence of salicylate and iodide.

What is claimed is:

1. A carbonate ion-selective membrane for use in a continuous flow analytical system comprising:
   (a) a dimensionally stable polymeric inert support material having dispersed therein:
      (i) a plasticizer effective to solubilize said support material;
      (ii) ion exchange means in the form of tetra-$C_7$–$C_9$ quarternary ammonium ions;
      (iii) an ionophore in the form of a higher alkyl-substituted fluoroacetophenone preferentially reactive with carbonate ions; and additionally
      (iv) a substance having hydrophobic a molecule effective to exclude ions other than carbonate ions, said molecule being selected from the group consisting of a 1-phenyldecane, a diphenyl ether, a dodecane and a butylbeuzene.

2. The membrane of claim 1 wherein the dimensionally stable polymeric inert support material is a vinyl chloride polymer.

3. The membrane of claim 2 wherein the vinyl chloride polymer is a vinyl chloride homopolymer.

4. The membrane of claim 3 wherein the polymer is a very high molecular weight poly (vinyl chloride).

5. The membrane of claim 1 wherein the plasticizer is an adipate.

6. The membrane of claim 5 wherein the adipate is di-(2-ethylhexyl) adipate.

7. The membrane of claim 1 wherein the plasticizer is selected from those effective to maximize the binding of carbonate ions with said $C_7$–$C_9$ quaternary ammonium ion.

8. The membrane of claim 1 wherein the fluoroacetophynenone is a para-substituted higher alkyl fluoroacetephenone.

9. The membrane of claim 1 wherein the ionophore is an orthosubstituted higher alkyl fluoroacetophenone.

10. The membrane of claim 1 wherein the higher alkyl fluoroacetophenone is a $C_{10}$–$C_{20}$ fluoroacetophenone.

11. The membrane of claim 10 wherein the fluoroacetophenone is selected from the group consisting of alpha-substituted trifluoroacetophenones.

12. The membrane of claim 1 wherein the $C_7$–$C_9$ quaternary ammonium ion is tetra-n-octyl quaternary ammonium.

13. The membrane of claim 1 wherein the hydrophobic molecule effective to exclude ions other than carbonate ion is at least a $C_{10}$ molecule.

14. The membrane of claim 13 wherein the hydrophobic molecule is a 1-phenyldecane.

15. The membrane of claim 13 wherein the hydrophobic molecule is a diphenyl ether.

16. The membrane of claim 13 wherein the hydrophobic molecule is a dodecane.

17. The membrane of claim 13 wherein the hydrophobic molecule is a butylbenzene.

18. A carbonate ion-selective electrode comprising an internal reference component in electrochemical contact with the membrane of claim 1.

19. The electrode of claim 18 which further comprises an internal electrolyte solution in fluid contact between said internal reference component and said membrane.

20. The electrode of claim 18 wherein the internal reference component is of an electroconductive material.

21. The electrode of claim 20 wherein the electroconductive material is of silver, gold, platinum, mercury or amalgams or mixtures thereof.

22. The electrode of claim 20 wherein the internal reference component is a silver structure of which at least a part is coated with a silver halide.

23. The electrode of claim 18 wherein the internal reference element is a pellet comprising silver chloride, silver sulfide, mercuric chloride or mercuric sulfide.

* * * * *